United States Patent
Nanbu

(10) Patent No.: US 6,774,620 B2
(45) Date of Patent: Aug. 10, 2004

(54) WAFER MAP DISPLAY APPARATUS AND METHOD FOR SEMICONDUCTOR TEST SYSTEM FOR DISPLAYING AN IMAGE OF WAFER AND IC CHIPS WITH OPTIMUM DISPLAY SIZE

(75) Inventor: Mitsue Nanbu, Tokyo (JP)

(73) Assignee: Advantest Corp, Tokyo (JP)

( * ) Notice: Subject to any disclaimer, the term of this patent is extended or adjusted under 35 U.S.C. 154(b) by 0 days.

(21) Appl. No.: 10/373,919

(22) Filed: Feb. 25, 2003

(65) Prior Publication Data

US 2003/0173990 A1 Sep. 18, 2003

Related U.S. Application Data

(63) Continuation-in-part of application No. 09/711,704, filed on Nov. 13, 2000, now Pat. No. 6,552,527.

(51) Int. Cl.[7] .............................................. G01R 15/08
(52) U.S. Cl. ..................................... 324/158.1; 324/765
(58) Field of Search .............................. 324/731, 158.1, 324/765; 382/145, 147; 356/394

(56) References Cited

U.S. PATENT DOCUMENTS

| | | | |
|---|---|---|---|
| 4,720,870 A | 1/1988 | Billiotte et al. | |
| 5,256,578 A | 10/1993 | Corley et al. | |
| 5,307,421 A | 4/1994 | Darboux et al. | |
| 5,671,165 A | * | 9/1997 | Tomimatu ..................... 702/94 |
| 6,421,122 B2 | * | 7/2002 | Nara et al. ................... 356/394 |

* cited by examiner

*Primary Examiner*—Vinh P. Nguyen
(74) *Attorney, Agent, or Firm*—Muramatsu & Associates

(57) ABSTRACT

A wafer map display apparatus and method for displaying an entire image of a semiconductor wafer and IC chips therein with an optimal display size within a specified window size. The wafer map display apparatus acquires window size information for displaying a wafer map of a semiconductor wafer under test in a specified window, and calculates a chip display size every time when receiving test results and XY address data of an IC chip that has been tested with use of all of XY address data of IC chips that have been tested, and renews the wafer map display based on the newest chip display size, thereby displaying all of the IC chips that have been tested and an overall semiconductor wafer under test with an optimum size within the specified window.

14 Claims, 8 Drawing Sheets

WAFER MAP DISPLAY APPARATUS AND METHOD FOR SEMICONDUCTOR TEST SYSTEM FOR DISPLAYING AN IMAGE OF WAFER AND IC CHIPS WITH OPTIMUM DISPLAY SIZE

This is a continuation-in-part of U.S. patent application Ser. No. 09/711,704 filed Nov. 13, 2000 now U.S. Pat No. 6,552,527.

FIELD OF THE INVENTION

This invention relates to a wafer map display apparatus and method for a semiconductor test system, and more particularly, to a wafer map display apparatus which is capable of displaying an entire image of a semiconductor wafer and IC chips therein with an optimal display size within a specified window size even when there is no information available in advance on the number of IC chips or locations of the IC chips on the wafer.

BACKGROUND OF THE INVENTION

A wafer map display apparatus is used in a semiconductor test system for displaying an image of each IC chip on a semiconductor wafer as well as overall characteristics of the wafer for easily and accurately observing the test results. The wafer map display apparatus provides important information for evaluating a semiconductor wafer from the standpoint of production yield and quality assurance in a semiconductor production process.

Because a display device (monitor) of a semiconductor test system is usually based on an operating system using "windows", such a wafer map display is also displayed on the display device in a manner similar to other application tools using the windows. Therefore, a size of the window for displaying the wafer map is not adjusted in an optimum manner for the wafer display but frequently changed based on the operating system and application tools.

An example of conventional technology involved in such a wafer map display apparatus is explained below with reference to FIGS. 4 and 5. First, an entire structure of the semiconductor test system is shown in FIG. 4. In the example of FIG. 4, the system includes a test system main frame, a test station, a wafer prober, a workstation WS, a wafer map display apparatus, an external input means (key board and mouse, etc.), a storage medium (floppy disc, CDROM, hard disc, etc.), and a display device (monitor).

On a semiconductor wafer such as a silicon wafer, a plurality of IC chips to be tested are aligned in a matrix manner. The wafer prober is a handling device that can load, test, and unload semiconductor wafers one by one continuously in combination with the test station of the semiconductor test system. One or more IC chips are tested at the same time by connecting probe pins of the wafer prober to contact pads (electrodes) on the IC chips to establish electrical connection between the IC chips and the semiconductor test system for electrical communication therebetween for the purpose of testing the IC chips.

In the following description, it is assumed that each IC chip is tested one by one for illustration purpose. Thus, during the test, the test result for each IC chip and the X-Y address of the IC chip on the semiconductor wafer are obtained by the semiconductor test system one by one and sent to the workstation WS.

The semiconductor test system that is composed of the test system main frame and the test station electronically communicates with the wafer prober through the test station, and tests the IC chips on the semiconductor wafer in a predetermined order. Every time when one IC chip is tested, the semiconductor test system sends the test result (pass/fail) information and category information of the particular IC chip to the workstation WS, along with the chip address information of the IC chip on the semiconductor wafer through a communication network or line.

Upon receiving the test result information (which includes the chip address information on the wafer, pass/fail information in the test result, and the category information) from the semiconductor test system, the workstation WS provides the received information to the wafer map display apparatus. The received information is also stored in the storage medium.

The display device is a monitor which displays the test results and other information in a window format. It is rare for the display device used for the wafer map display of such a semiconductor test system that is set to a single window such as shown in FIG. 5A. Rather, as shown in FIG. 5B, the wafer map display screen is shown on the display device along with other windows of other application tools. Therefore, the window size for the wafer map display varies depending on the size of the other window applications. Moreover, the user can change the window size of the wafer map display through an input means such as a mouse.

In the conventional wafer map display application, the display size for each IC chip is fixed. Because of this, the window size required for displaying an entire semiconductor wafer varies when displaying a wafer of different number of IC chips or a wafer having different XY address alignment of IC chips. An example of a manner of displaying each IC chip is a color display such as using green and red based on the pass/fail information or a color display based on the category information.

An example of wafer map displays in the conventional technology is shown in FIGS. 5A and 5B. First, in the example of large window size (window A) in FIG. 5A, it displays all of the IC chips within the window A. However, since the display size of each IC chip is fixed, even though the window A of FIG. 5A is large enough, the wafer map of the overall semiconductor wafer W is displayed much smaller than the size of the window A. Thus, the display example of FIG. 5A has a large portion of unused space, as shown by an area C. In other words, the overall semiconductor wafer is not displayed in the optimal size.

FIG. 5B hows another display example in the conventional technology in which the display monitor shows windows D, F and G of smaller sizes. The window D shows images of IC chips CH and the semiconductor wafer W wherein not all of the IC chips CH (or entire semiconductor wafer W) are displayed within the window D. Therefore, in this example, the test results of the entire semiconductor wafer are not observed in one screen, and the user has to use a pointing device such as a mouse to scroll the display. Moreover, in this conventional example, it is not possible to easily observe the manner of distribution of characteristics of the IC chips over the entire wafer.

As mentioned above, the conventional wafer map display technology has a drawback in which it is not able to display the IC chips in an optimal size because the chip display size is fixed. Moreover, although the window size required for displaying the entire wafer varies when displaying a wafer of different size, or a wafer of different number of chips or a wafer with different chip alignment, the wafer map display cannot adjust the overall display size of the wafer because the chip display size is fixed. Furthermore, when the window size that displays the wafer map is small, it is burdensome and inconvenient for the user to evaluate the wafer and chips since the entire wafer and all of the chips cannot be displayed on the monitor at the same time.

SUMMARY OF THE INVENTION

Therefore, it is an object of the present intention to provide a wafer map display apparatus and method that is capable of displaying an entire wafer image with an optimal chip display size depending on the number of chips and the XY address information of the chips on the semiconductor wafer relative to the window size in the wafer map display without causing a substantial unused area in the window.

It is another object of the present invention to provide a wafer map display apparatus and method which is capable of calculating and changing an optimal chip display size to display an image of all of the IC chips that have been tested and an overall image of the semiconductor wafer within the specified window size every time when the test result of each IC chip is received from the semiconductor test system.

It is a further object of the present invention to provide a wafer map display apparatus and method of improved test efficiency and accuracy by displaying an image of the IC chips that have been tested with a maximum available size within the specified window size every time when the test result of each IC chip is produced by the semiconductor test system.

To achieve the above objectives, the first aspect of the present invention is a wafer map display apparatus for a semiconductor test system for testing semiconductor devices by displaying an image of IC chips on a semiconductor wafer based on test results. The wafer map display apparatus includes a window manager which is a display controller established based on an operating system of a personal computer or a workstation for displaying a wafer map of a semiconductor wafer under test in a specified window, means for acquiring window size information, means for acquiring IC chip information, means for storing the semiconductor wafer information, means for calculating a chip display size, and means for renewing the wafer map display.

An interface unit which is typically a format converter for window manager for converting the format of the data from the window manager to match with that of the units in the wafer map display apparatus. The interface unit periodically receives the window size information from the window manager and if the window size is changed, the window size information is sent to the calculating means for calculating a chip display size. The semiconductor test system communicates with the wafer map display apparatus and sends the IC chip information to the interface unit every time when an IC chip is tested.

Upon acquiring the IC chip information, an interface unit which is typically a format converter for test system for converting the format of the data from the semiconductor test system to match with that of the units in the wafer map display apparatus. The interface unit sends the information to the calculating means for calculating a chip display size and the chip information may be stored in the storing means in order to display the IC chip information on each image of IC chips on a wafer map. The calculating means determines a new size of IC chip display using both the window size and the XY address data. Then, the wafer map renewing means receives the new size of the chip display and the window manager refreshes the display screen to display a new wafer map based on the new size of the chip display.

Preferably, the chip display size is calculated every time when the window size information from the window manager is changed based on the XY address data of all of the IC chips that have been tested so that the images of the IC chips and the semiconductor wafer under test are displayed with a sufficiently large size or a maximum available size within the window size specified by the window manager. Alternatively, the chip display size is determined based on the window size information from the window manager and the chip display size obtained in the previous tests for the same kind of semiconductor wafer.

In the wafer map display apparatus, the semiconductor test system is able to test a plurality of semiconductor wafers in parallel at the same time and the window manager provides window size information to the window size acquiring means for displaying a plurality of windows on the wafer map display apparatus, whereby displaying a plurality of windows each showing a set of IC chips and the semiconductor wafer corresponding to the specified size of the window.

Another aspect of the present invention is a method of displaying a wafer map which is an image of IC chips on a semiconductor wafer based on test results to be implemented by a semiconductor test system for testing a semiconductor wafer. The method includes the steps of acquiring window size information from the window manager for displaying the wafer map of a semiconductor wafer under test in a specified window, calculating a chip display size every time when XY address data of an IC chip that has been tested is received from the semiconductor test system with use of all of XY address data of all of IC chips that have been tested up to the present, an renewing the wafer map display based on the newest chip display size determined by the calculating step, thereby displaying all of the IC chips that have been tested and an overall semiconductor wafer under test with an optimum size within the specified window.

Preferably, the step of calculating the chip display size includes a process of calculating the chip display size every time when the window size information from the window manager is changed based on the XY address data of all of the IC chips that have been tested so that the images of the IC chips and the semiconductor wafer under test are displayed with sufficiently large size within the window size specified by the window manager.

Alternatively, the step of calculating the chip display size includes a process of determining the chip display size based on the window size information from the window manager and the chip display size obtained in the previous test for the same kind of semiconductor wafer. When the chip display size is determined based on the previous test results of the other wafer, an IC chip is displayed with a size suitable for all of the IC chips on the semiconductor wafer can be displayed in one specified window even when the number of tested IC chips is substantially smaller than the overall number of IC chips on the semiconductor wafer under test.

A further aspect of the present invention is a zoom feature. In the present invention, if the number of the IC chips on wafer map is increased, the IC chip information on each IC chip cannot easily be read. In order to overcome the difficulty, the wafer map display apparatus of the present invention provides a zoom feature in which a predetermined or selected IC chip is enlarged on the display screen. For example, when a zoom command is received, the newest IC chip that has been tested is automatically selected and displayed in a zoom mode. If a zoom command with particular XY address data is received, the IC chip on the particular XY address may be displayed in the zoom mode.

According to the present invention, the wafer map display apparatus and method is capable of displaying the IC chips and semiconductor wafer with optimum size such as a maximum available size in the window even when the number of IC chips or XY chip address information is unknown in advance. The wafer map display apparatus and method of the present invention calculates the chip display size based on the test result information and displays the IC chips with colors and letters and the semiconductor wafer based on the calculated chip display size in an optimal size regardless of the number of IC chips within the window size. Therefore, the present invention substantially improves efficiency and accuracy of evaluating the IC chips and semiconductor wafers.

DETAILED DESCRIPTION OF THE INVENTION

Figure 1A:
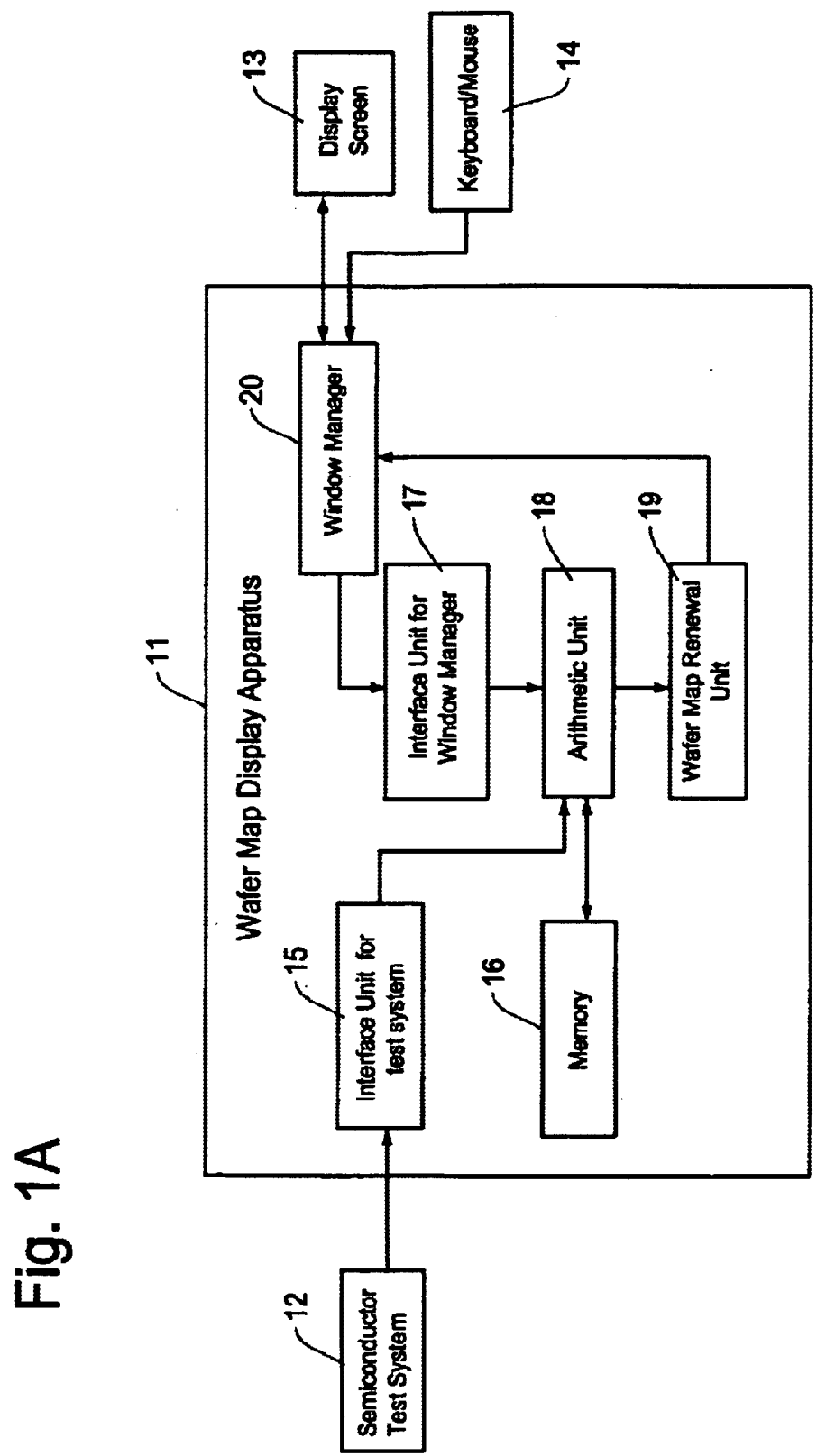
FIG. 1A is a block diagram showing an example of structure in the wafer map display apparatus of the present invention.
Figure 1B:
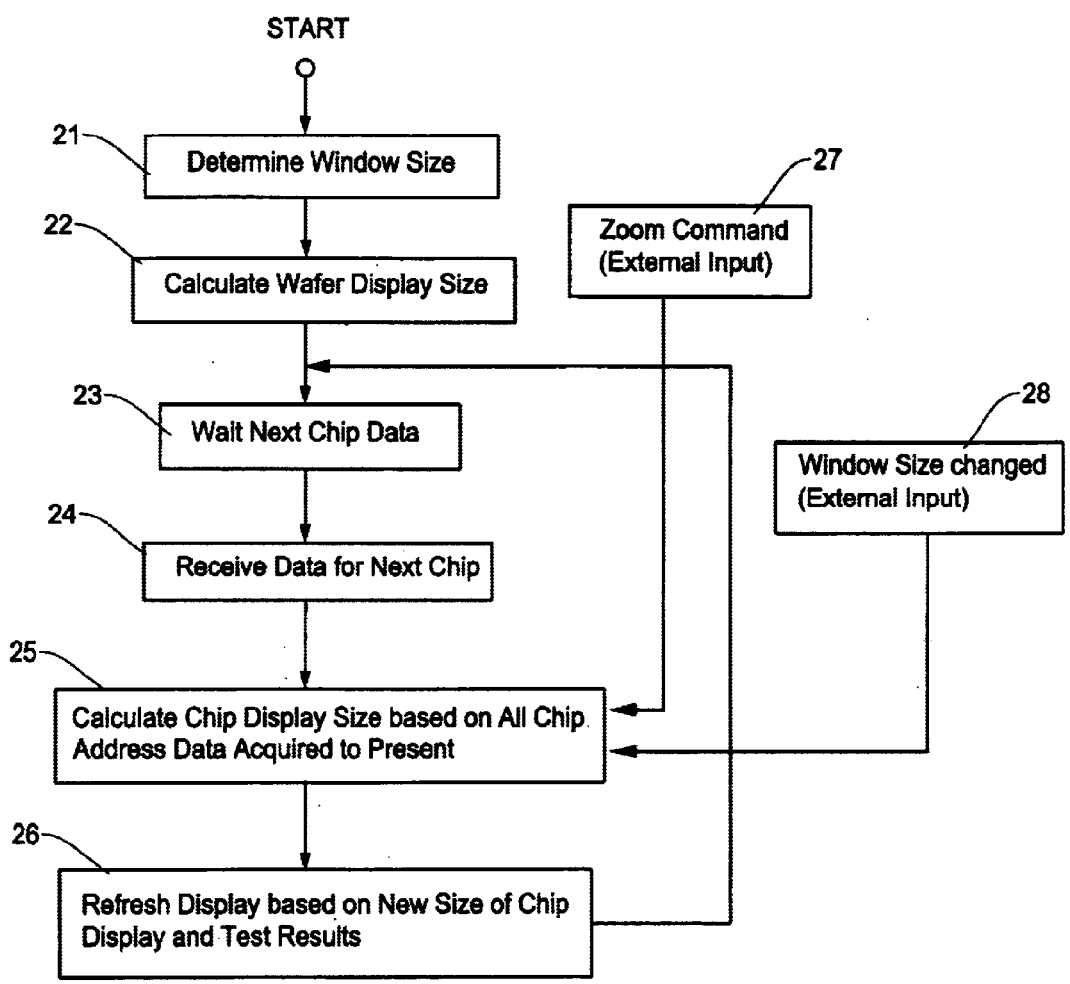
FIG. 1B is a flow chart showing an example of operational procedure for displaying the wafer map adjusted to the window size in the present invention.
Figure 1C:
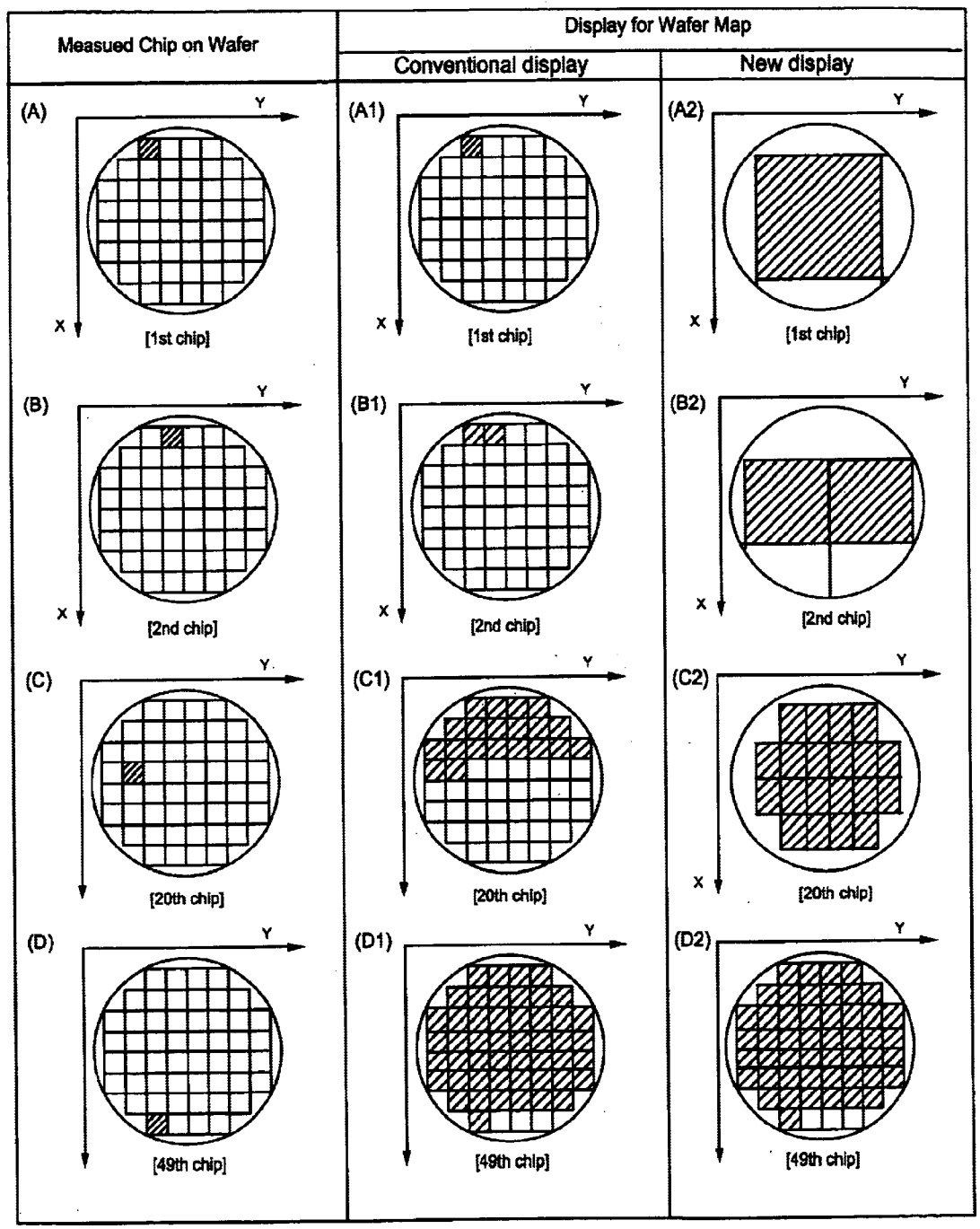
FIG. 1C is a table showing examples of display for comparing the conventional wafer map display and the new wafer map display in the present invention.
Figure 1D:
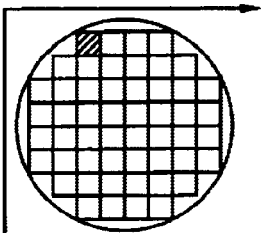
FIG. 1D is a table showing examples of a zoom feature of the present invention.

Preferred embodiments of the present invention will be described in the following with reference to the accompanying drawings. The embodiments of the present invention are shown in FIGS. 1–3 wherein FIG. 1A is a block diagram showing an example of structure in the wafer map display apparatus, FIG. 1B is a flow chart showing an example of operational procedure for displaying the wafer map adjusted to the window size, FIG. 1C shows display examples comparing the conventional technology and the new technology, and FIG. 1D shows examples of a zoom feature for enlarging the display size of the selected IC chip. FIGS. 2A–2E show examples of wafer map display with an optimal IC chip display size for different number of IC chips, and FIG. 3 shows an example of wafer map display with a plurality of windows in which an entire semiconductor wafer is displayed in one of the windows.

Here, it is assumed that test result information of an IC chip is transferred from the semiconductor test system to the wafer map display apparatus each time when the test result is obtained for one or more IC chips. It is also assumed that the information regarding the number of IC chips in the entire semiconductor wafer and the XY alignment (XY address) of the IC chips in the semiconductor wafer is normally not necessary. Since the number of IC chips that are to be displayed in the window on the display monitor and the locations of the IC chip are unknown to the wafer map display application, the chip display size is also undefined at the start of the wafer map display process.

Referring to FIGS. 1A–1D and FIG. 2, a structure and operations of wafer map display apparatus in the present invention are described. As shown in FIG. 1A, the wafer map display apparatus 11 is comprised of an interface unit 15 for a semiconductor test system, a memory 16, an interface unit 17 for a window manager, an arithmetic unit 18, a wafer map renewal unit 19 a window manager 20. The window manager 20 is connected to a display 13 and an input device such as keyboard/mouse 14.

Typically, the window manager 20, display 13 and keyboard/mouse 14 constitute a part of a window based computer such as a workstation WS or a personal computer to control an overall window display operation of the wafer map display apparatus based on data from a semiconductor test using an architecture different from that of the personal computer or workstation. In other words, the window manager 20 is a display controller for controlling a display operation of a personal computer or a workstation using a general purpose window based operating system such as "Window", "Window NT", "UNIX" and the like. Such a display controller is well known in the art since he operating systems noted above are open resources and widely used in the industry.

Further, the interface units 15 and 17 are basically format converters for matching the data formats between two different systems such as semiconductor test system and the wafer map display apparatus or between the window based computer and the wafer map display apparatus as in the case of the present invention. Such a format converter is well known in the art since any two different systems need a format converter when connecting with one another to transfer the data from one to the other. The wafer map renewal unit 19 is basically a data buffer to receive the chip size information calculated by the arithmetic unit 18 and transfers the chip size information to the window manager 20.

The interface unit 17 for window manager acquires the window size information from the window manager 20. Then, the window size information is transferred to the arithmetic unit 18. Since the interface unit 17 periodically receives the size information from the window manager 20, new window size information can be sent to the arithmetic unit 18 immediately after the window size is changed.

Upon starting the test for IC chips on a semiconductor wafer, a semiconductor test system 12 communicates with the wafer map display apparatus 11 and sends the IC chip information including an XY address on the wafer, test results (pass/fail data) and category information of the IC chip to the interface unit 15. Upon acquiring the IC chip information, the interface unit 15 adjusts the data format and sends the IC chip information to the arithmetic unit 18 for calculating a chip display size. The IC chip information may be stored in the memory 16 in order to display the IC chip information on each IC chip on a wafer map each time when refreshing a screen of the wafer map. The memory 16 may also be used for storing other information such as address information of overall IC chips on the wafer, information and test results of previous semiconductor wafers, etc. The arithmetic unit 18 calculates a wafer display size to determine the overall size of the semiconductor wafer to be fit to the window size by using both the window size information and the XY address information.

If the window size is changed by a user through the keyboard/mouse 14 before the next IC chip information is acquired, the new window size information is transferred to the arithmetic unit 18 via the interface unit 17 which adjusts the data format. Then, the arithmetic unit 18 determines a new size of chip display based on both the new window size and the XY address data information of the newest IC chip to have been tested. For example, the arithmetic unit 18 is able to determine the number of IC chips that have been tested at a particular time based on the XY address data received and calculates the chip display size such as the maximum available chip display size in the specified window size.

The wafer map renewal unit 19 receives the new size of the chip display from the arithmetic unit 18, acquires all the IC chip information of chips that have been tested which is stored in the memory 16, and transfers the information to the window manager 20. The window manager 20 refreshes the display screen 13 in order to display the new wafer map based on the new size of the chip display. At the same time, the window manager 20 also refreshes the IC chip information such as test results (pass/fail data) and category information on the image of each IC chip.

With reference to FIGS. 1A–1D and FIGS. 2A–2F, an example of operational process of the present invention is described in detail. Here, FIG. 1B is a flow chart of the operational process, FIG. 1C is a diagram showing display examples or comparing the conventional wafer map apparatus and the wafer map display apparatus of the present invention, and FIG. 1D shows display examples in a zoom mode of the wafer map display apparatus of the present invention. In FIGS. 1C and 1D, the shaded areas indicate that the corresponding IC chips are already tested. FIGS. 2A–2F show similar examples of wafer map display with characters of the IC chip information.

As shown in FIG. 1B, the size of the window is determined in the step 21 which is specified by the user or automatically by the widow manager 20 (display controller for personal computer or workstation WS). Namely, the window size is defined for the wafer map display apparatus by the window size information from the window manager 20. In the block diagram of FIG. 1A, the window size information is sent to the arithmetic unit 18 through the interface unit 17.

In step 22, the arithmetic unit 18 calculates the wafer display size to determine the overall size of the semiconductor wafer to be fit to the window based on the window size information obtained in the step 21. Thus, the overall shape of the semiconductor wafer is displayed with the maximum size within the specified window. Further, one or more IC chips may be displayed within the image of this semiconductor wafer. In the present invention, typically, the IC chips that have been tested are displayed within the image of the semiconductor wafer with the maximum available size as will be described later.

In step 23, the process waits for the information concerning the next IC chip from the semiconductor test system. Typically, such a waiting time is from few seconds to several minutes during which the semiconductor test system supplies test signals to the IC chip and evaluates the response outputs of the IC chip. During this waiting period, if the window size is changed by an external input in step 28 such as a mouse or a keyboard, the wafer map display apparatus retrieves the window size information again, the new wafer size will be determined by the arithmetic unit 18 as in the step 21.

In step 24, the wafer map display process retrieves IC chip information regarding one IC chip on the semiconductor wafer from the semiconductor test system. Such IC chip information includes the test results (pass/fail and test category and fail category and the like) and the IC chip address (XY address on the semiconductor wafer) information of the IC chip that has been tested. The information is received by the window manager 20 (display controller for personal computer or workstation WS).

Referring to step 25, the window manger 20 and the arithmetic unit 18 interact to determine an IC chip display size by using all of the chip XY address information received by that time. The IC chip display size is determined in such a way that all of the IC chips that have been tested can be displayed with a sufficiently large size, preferably with the maximum available size on the wafer image within the specified window size. In other words, the IC chip display size varies depending on the number of IC chips that have been tested so far.

Thus, according to this procedure, in FIG. 1C, when the first IC chip is tested (example A), the wafer map display apparatus of the present invention displays one large IC chip (example A2) with the maximum display size. In the conventional technology, since it is designed to display the overall chips on the wafer, the first IC chip is displayed with all the other IC chips, i.e., with small size (example A1). Similarly, when the second IC chip is tested (example B), the wafer map display apparatus of the present invention displays two large IC chips (example B2) with the maximum display size. In the conventional technology, the first and second IC chips are displayed with all the other IC chips, i.e., the same small size (example B1).

For example, when the twentieth IC chip is tested (example C), the wafer map display apparatus of the present invention displays twenty IC chips (example C2) with the maximum possible display size while in the conventional technology, the display size of each chip is unchanged (C1). When almost all of the IC chips are tested (example D), the IC chip display size is about the same in the conventional technology (example D1) and the present invention (example D2). In this manner, depending on the number of IC chips that have been tested, the wafer map display apparatus of the present invention changes the size of each IC chip and displays the tested IC chips.

When the number of the IC chips on the wafer map is increased, the chip display size is decreased, thus, the IC chip information on each IC chip cannot easily be observed. In order to overcome this difficulty, the wafer map display apparatus of the present invention is designed to enlarge a selected IC chip. An example of such a zoom function is shown in FIG. 1D in the right column. At step 27, when a zoom command is made by a user through the window manager by selecting a particular IC chip by a pointing device (ex. mouse 14, or touch screen), the wafer map display apparatus enlarges the image of the selected IC chip.

When the number of tested IC chips is small, the display apparatus displays the tested IC chips with the maximum display size, thus, the zoom function is not so useful. Thus, the zoom feature is not available in the upper two examples of FIG. 1D. However, as noted above, when the number of IC chips becomes large, the display size of each IC chip that has been tested becomes small as in the lower two examples of FIG. 1D. The zoom function is useful in such a situation to observe the selected IC chip in detail.

For example, the user can select a particular IC chip on the display through a touch screen, mouse or keyboard to be displayed in the zoom mode. Various other methods can be available to select a particular IC chip to be enlarged, such as defining the XY address, or a failed IC chip, etc. Alternatively, the wafer map display apparatus automatically selects the newest IC chip that has been tested and displays the IC chip in the enlarged image such as the 20th tested IC chip or the 49th tested IC chip in FIG. 1D.

In step 26, the process refreshes all of the display with the new display based on the test result including the category information that have been acquired up to the present corresponding to the locations in the wafer defined by the XY address data of the IC chips. Such test results may be displayed with use of colors or characters for illustrating the "pass/fail" and/or "fail and test category" such as shown in FIGS. 2A–2F.

Figure 2A:
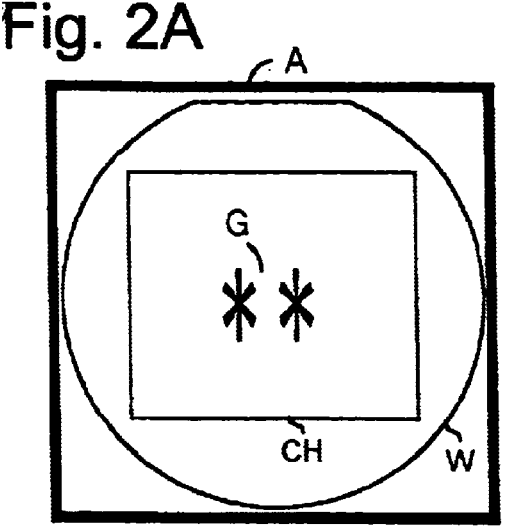
FIGS. 2A–2F are diagrams showing examples of wafer map display with an optimal IC chip display size in a step-by-step manner in accordance with the present invention.
Figure 2B:
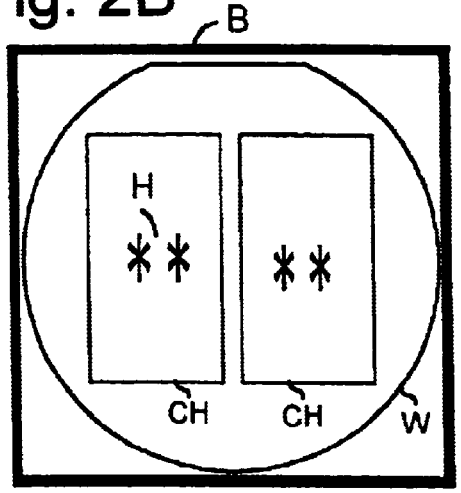
Figure 2C:
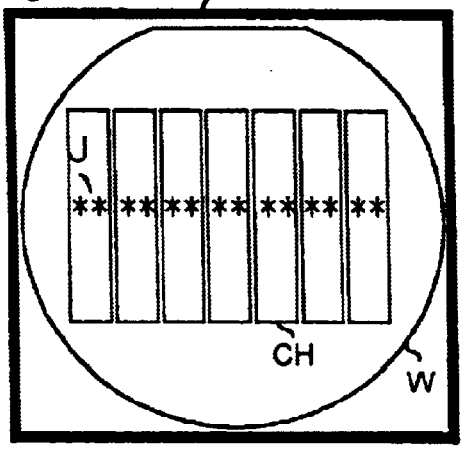
Figure 2D:
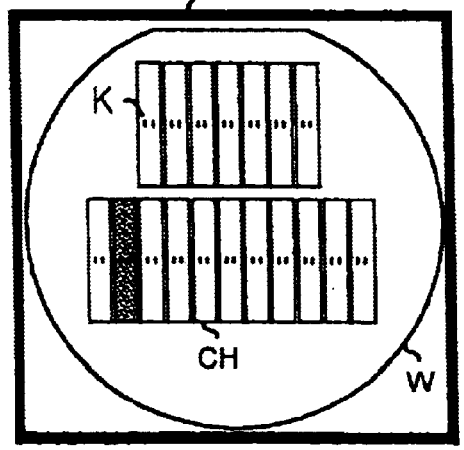
Figure 2E:
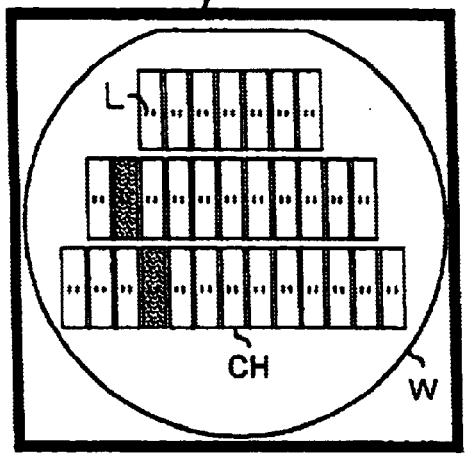
Figure 2F:
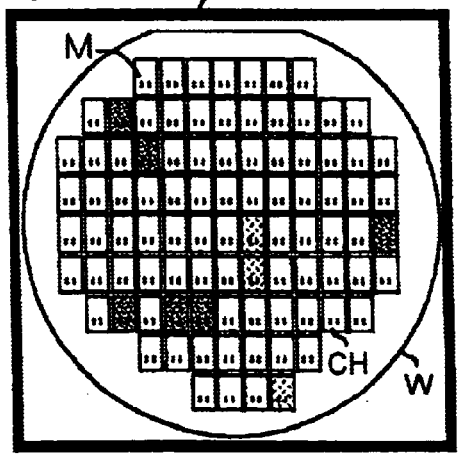
Figure 3:
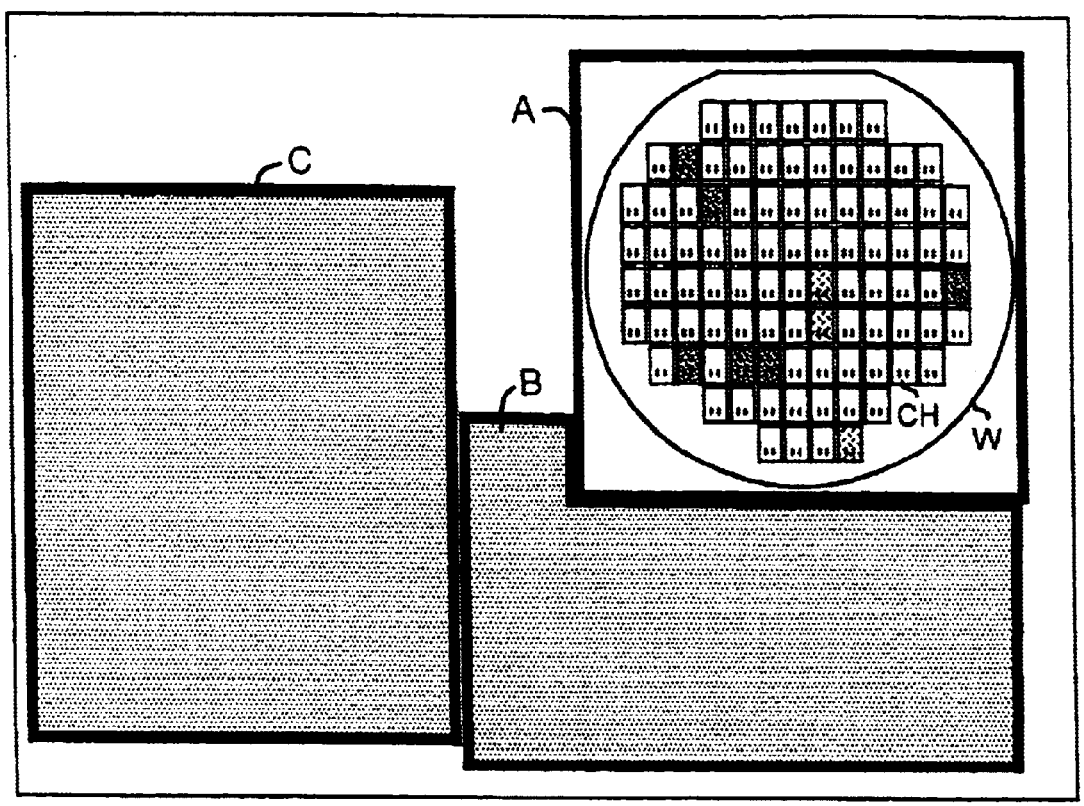
FIG. 3 is a diagram showing an example of wafer map display in the present invention with a plurality of windows of small size in which an entire semiconductor wafer is displayed in one of the windows.
Figure 4:
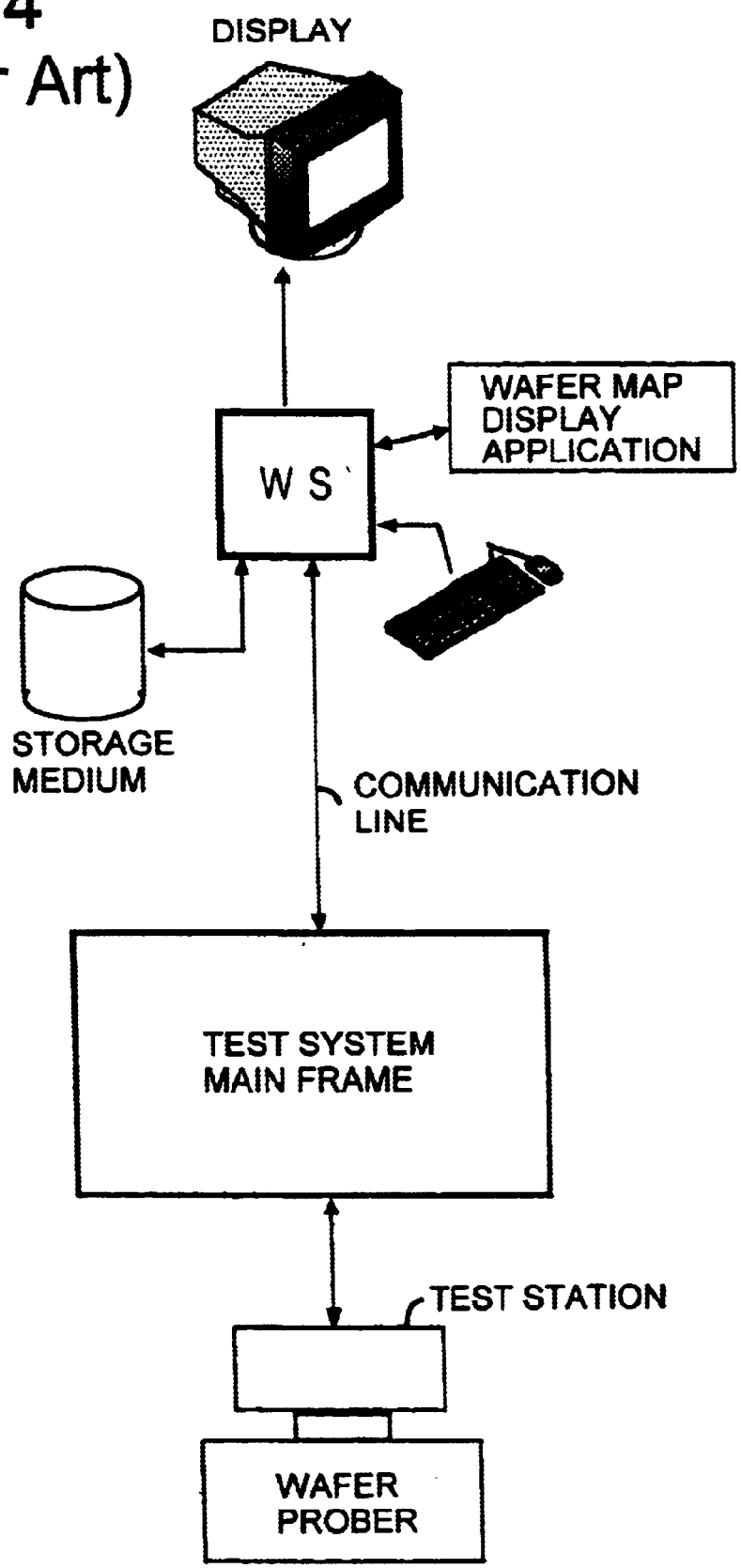
FIG. 4 is a schematic diagram showing an example of semiconductor test system including a workstation and a display device where a test station and a wafer prober are connected with one another.
Figure 5A:
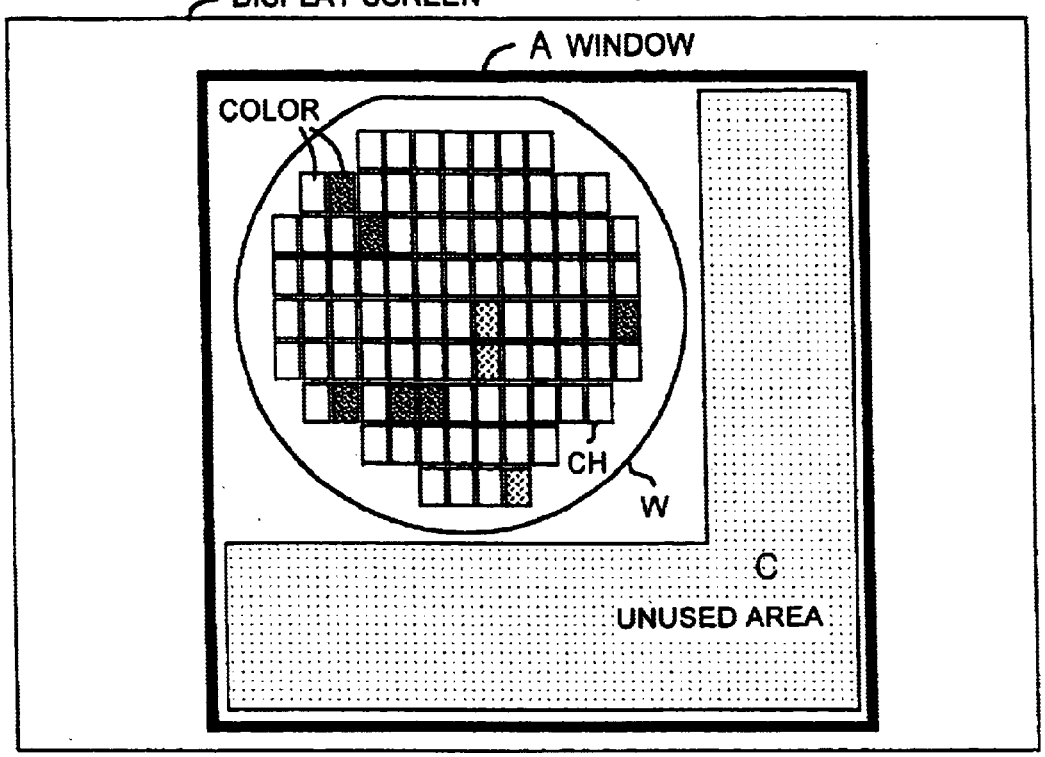
FIGS. 5A and 5B are diagrams showing an example of wafer map display with different sizes of window in the conventional technology.
Figure 5B:
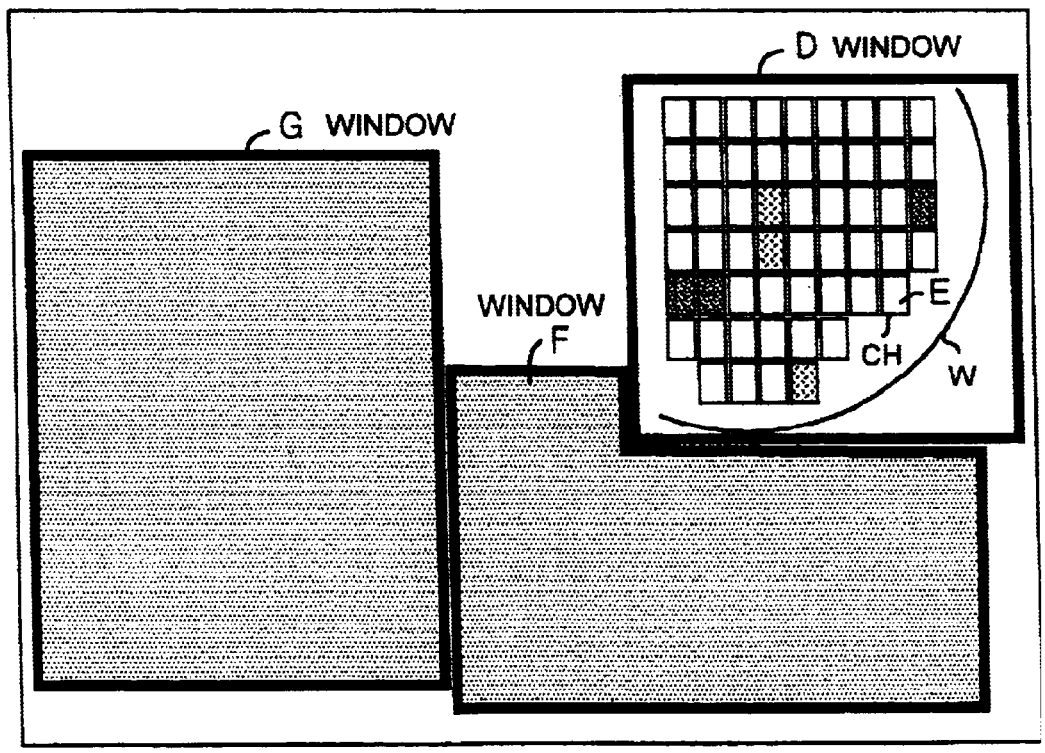

FIGS. 2A–2F are diagrams showing examples of wafer map display with an optimal IC chip display size in a step-by-step manner in accordance with the present invention. As shown in FIGS. 2A–2F and as described in the foregoing, the size of each IC chip becomes smaller as the number of IC chips on the wafer is increased. Marks, "G", "H", "J", "K", "L" and "M" indicate characters describing the information on each IC chip. The characters on the IC chip can be easily read since the IC chip information on the IC chip is also displayed in the maximum available size (FIGS. 2A–2B).

According to the procedure and display examples of FIGS. 1B–1D and FIGS. 2A–2F, the semiconductor wafer with all of the IC chips tested so far can be displayed with the maximum size available for the window size without causing an unused area in the window. Thus, as shown in FIG. 3, even with a rather small window size, all of the IC chips that have been tested can be displayed within the specified window size. Further as shown in FIG. 3, the wafer map display with an optimal size can be displayed corresponding to the window size.

An actual implementation of the present invention is not limited to the aforementioned example but can be implemented in a modified manner as well. For example, IC chips under the mass production may involve the same wafer size, same number of IC chips on the wafer and the same XY addresses on the wafer. Thus, when this information is known in advance, the same display data such as the IC chip display size data obtained concerning the previous semiconductor wafer can be used for displaying the wafer map display for the remaining wafers and IC chips. Further, since the number of IC chips and the addresses on the wafer are known, even when only the first IC chip are tested, such a test result can be displayed in the manner and size of FIG. 2E, thereby achieving an image of actual relationship between the IC chips and semiconductor wafer.

Moreover, when receiving the test result information for all of the IC chips on the wafer stored in the storage medium, rather than one by one, the positional information for all of the IC chips are ready at the first stage of displaying the wafer map display. Therefore, even when displaying only the first IC chip on the wafer, the first IC chip can be displayed with the final IC chip display size of FIG. 2E, thereby achieving an image of actual relationship between the IC chips and semiconductor wafer.

Furthermore, in the case where two or more wafer probers are used and thus IC chips on two or more semiconductor wafers are tested in parallel at the same time, the wafer map display of the present invention can display two or more windows corresponding to the number of wafers to display the IC ships and wafers in the corresponding windows with optimum sizes at the same time.

As has been foregoing, the wafer map display apparatus and method of the present invention is capable of displaying the IC chips and semiconductor wafer with optimum size in the window even when the number of IC chips or XY chip address information is unknown in advance. The wafer map display apparatus and method of the present invention calculates the IC chip display size based on the test result information and displays the IC chips with letters and colors and the semiconductor wafer based on the calculated IC chip display size in an optimal size such as maximum available size based corresponding to the number of IC chips within the window size. Therefore, the present invention substantially improves efficiency and accuracy of evaluating the IC chips and semiconductor wafers.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A wafer map display apparatus for a semiconductor test system for testing semiconductor devices by displaying an image of IC chips on a semiconductor wafer based on test results, comprising:

means for controlling a display device for displaying a wafer map of a semiconductor wafer under test on a specified window;

means for acquiring IC chip information from the semiconductor test system, wherein the IC chip information includes XY address data of an IC chip on the semiconductor wafer under test;

means for calculating a chip display size every time when XY address data of an IC chip that has been tested is received from the semiconductor test system with use of all of XY address data of IC chips acquired up to present and window size information from the means for controlling the display device; and means for renewing the wafer map display every time when a new IC chip is tested based on the chip display size determined by the means for calculating the chip display size, thereby displaying all of the IC chips that have been tested with a maximum available size on an image of the semiconductor wafer within the specified window.

2. A wafer map display apparatus for a semiconductor test system as defined in claim 1, wherein the means for calculating the chip display size determines the IC chip display size every time when the window size information from the means, for controlling the display device is changed based on the XY address data of all of the IC chips that have been tested so that the images of the IC chips and the semiconductor wafer under test are displayed with the maximum size within the window size specified by the means for controlling the display device.

3. A wafer map display apparatus for a semiconductor test system as defined in claim 1, wherein the means for calculating the chip display size determines the IC chip display size based on the window size information from the means for controlling the display device and the IC chip display size obtained in previous tests for the same kind of semiconductor wafer stored in a memory.

4. A wafer map display apparatus for a semiconductor test system as defined in claim 1, wherein said means for controlling the display device provides window size information of two or more windows, when a plurality of semiconductor wafers are tested in parallel at the same time, to the means for calculating the chip display size, whereby a plurality of images are displayed each showing the IC chips with the maximum size and the semiconductor wafer for each window corresponding to the size of the window.

5. A wafer map display apparatus for a semiconductor test system as defined in claim 1, wherein the means for calculating the IC chip display size determines the IC chip display size of a selected IC chip in a zoom mode after receiving a zoom command through he means for controlling the display device.

6. A wafer map display apparatus for a semiconductor test system as defined in claim 5, wherein a newest IC chip that has been tested is automatically selected for the zoom mode, thereby displaying an image of the newest IC chip with an enlarged size.

7. A wafer map display apparatus for a semiconductor test system as defined in claim 1, wherein test results and a fail category of the IC chip that has been tested are displayed on the image of each IC chip.

8. A wafer map display for illustrating an image of IC chips on a semiconductor wafer based on test results made by a semiconductor test system, comprising:

a window for displaying a wafer map of a semiconductor wafer under test therein where the window is specified by a window based computer;

means for displaying a semiconductor wafer image within the specified window for illustrating the semiconductor wafer under test;

means for aligning IC chip images on the semiconductor wafer image based on IC chip information from the semiconductor test system where the IC chip information includes XY address data of an IC chip on the semiconductor wafer under test;

means for adjusting a chip display size of the IC chip image every time when XY address data of an IC chip that has been tested is received from the semiconductor test system with use of the XY address data of IC chips acquired up to present; and means for renewing the IC chip images every time when a new IC chip is tested in such a way to display all of the IC chips that have been tested with a maximum available size on the image of the semiconductor wafer within the specified window.

9. A wafer map display as defined in claim 8, wherein said means for adjusting the chip display size determines the chip display size every time when window size information from the window based computer is changed based on the XY address data of all of the IC chips that have been tested so that the images of the IC chips and the semiconductor wafer under test are displayed with the maximum size within the window size specified by the window based computer.

10. A wafer map display as defined in claim 8, wherein said means for adjusting the chip display size determines the chip display size based on window size information from the window based computer and the IC chip display size obtained in previous tests for the same kind of semiconductor wafer stored in a memory.

11. A wafer map display as defined in claim 8, wherein said window based computer produces window size information of two or more windows, when a plurality of semiconductor wafers are tested in parallel at the same time, for calculating the chip display size, thereby displaying a plurality of wafer map images each showing the IC chips that have been tested with the maximum size and the semiconductor wafer with the maximum size available for each window.

12. A wafer map display for a semiconductor test system as defined in claim 8, further comprising means for increasing the IC chip display size of a selected IC chip, thereby displaying an enlarged image of the selected IC chip in a zoom mode when a zoom command is received through the window based computer.

13. A wafer map display for a semiconductor test system as defined in claim 12, wherein said means for increasing the IC chip display size automatically selects a newest IC chip that has been tested for the zoom mode, thereby displaying an enlarged image of the newest IC chip.

14. A wafer map display as defined in claim 8, wherein test results and a fail category of the IC chip that has been tested are displayed on the image of each IC chip.

* * * * *